(12) United States Patent
Sims et al.

(10) Patent No.: US 11,350,982 B2
(45) Date of Patent: Jun. 7, 2022

(54) ELECTROSURGICAL FORCEPS

(71) Applicant: COVIDIEN LP, Mansfield, MA (US)

(72) Inventors: Grant T. Sims, Boulder, CO (US);
Kelley D. Goodman, Erie, CO (US);
Craig V. Krastins, Arvada, CO (US);
Robert F. Mccullough, Jr., Boulder, CO (US); Jennifer L. Rich, Parker, CO (US); Daniel W. Mercier, Erie, CO (US)

(73) Assignee: Covidien LP, Mansfield, MA (US)

(*) Notice: Subject to any disclaimer, the term of this patent is extended or adjusted under 35 U.S.C. 154(b) by 628 days.

(21) Appl. No.: 16/210,218

(22) Filed: Dec. 5, 2018

(65) Prior Publication Data

US 2020/0179035 A1 Jun. 11, 2020

(51) Int. Cl.
*A61B 18/14* (2006.01)
*A61B 18/08* (2006.01)
*A61B 18/00* (2006.01)
*A61B 18/12* (2006.01)

(52) U.S. Cl.
CPC ........ *A61B 18/1445* (2013.01); *A61B 18/085* (2013.01); *A61B 18/1206* (2013.01); *A61B 18/1492* (2013.01); *A61B 2018/0063* (2013.01); *A61B 2018/00577* (2013.01); *A61B 2018/00589* (2013.01); *A61B 2018/00601* (2013.01); *A61B 2018/00607* (2013.01); *A61B 2018/146* (2013.01)

(58) Field of Classification Search
CPC ....... A61B 2017/320074; A61B 2017/320075; A61B 2018/1412; A61B 2018/1452; A61B 2018/1455; A61B 2018/146; A61B 18/045; A61B 2018/1457
See application file for complete search history.

(56) References Cited

U.S. PATENT DOCUMENTS

| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| 4,763,669 | A | 8/1988 | Jaeger |
| D298,353 | S | 11/1988 | Manno |

(Continued)

FOREIGN PATENT DOCUMENTS

| CN | 201299462 Y | 9/2009 |
| CN | 202086577 U | 12/2011 |

(Continued)

OTHER PUBLICATIONS

Manufacturing_Materials_and_Processing proof of date (Year: 2021).*

(Continued)

*Primary Examiner* — Linda C Dvorak
*Assistant Examiner* — Nicholas S Borsch

(57) ABSTRACT

An electrosurgical forceps includes first and second shaft members pivotably coupled to one another via a pivot member such that pivoting of the first and second shaft members between spaced-apart and approximated positions pivots jaw members thereof between open and closed positions. A knife is translatable between retracted and extended positions. The knife has a stop to prevent distal movement of the knife beyond the extended position.

4 Claims, 5 Drawing Sheets

(56) References Cited

U.S. PATENT DOCUMENTS

| | | | |
|---|---|---|---|
| D299,413 S | 1/1989 | DeCarolis | |
| 5,100,420 A | 3/1992 | Green et al. | |
| 5,258,001 A | 11/1993 | Corman | |
| D343,453 S | 1/1994 | Noda | |
| 5,304,203 A | 4/1994 | El-Mallawany et al. | |
| D348,930 S | 7/1994 | Olson | |
| D349,341 S | 8/1994 | Lichtman et al. | |
| 5,344,424 A | 9/1994 | Roberts et al. | |
| D354,564 S | 1/1995 | Medema | |
| D358,887 S | 5/1995 | Feinberg | |
| 5,496,314 A * | 3/1996 | Eggers | A61B 18/082 606/29 |
| 5,540,685 A | 7/1996 | Parins et al. | |
| 5,578,052 A | 11/1996 | Koros et al. | |
| 5,611,808 A | 3/1997 | Hossain et al. | |
| 5,618,294 A | 4/1997 | Aust et al. | |
| D384,413 S | 9/1997 | Zlock et al. | |
| 5,665,100 A | 9/1997 | Yoon | |
| 5,752,644 A | 5/1998 | Bolanos et al. | |
| H1745 H | 8/1998 | Paraschac | |
| 5,814,043 A | 9/1998 | Shapeton | |
| D402,028 S | 12/1998 | Grimm et al. | |
| D408,018 S | 4/1999 | McNaughton | |
| 5,913,874 A | 6/1999 | Berns et al. | |
| 5,960,544 A | 10/1999 | Beyers | |
| D416,089 S | 11/1999 | Barton et al. | |
| 6,050,996 A | 4/2000 | Schmaltz et al. | |
| D424,694 S | 5/2000 | Tetzlaff et al. | |
| D425,201 S | 5/2000 | Tetzlaff et al. | |
| H1904 H | 10/2000 | Yates et al. | |
| 6,293,954 B1 | 9/2001 | Fogarty et al. | |
| D449,886 S | 10/2001 | Tetzlaff et al. | |
| 6,329,778 B1 | 12/2001 | Culp et al. | |
| 6,334,861 B1 | 1/2002 | Chandler et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,406,485 B1 | 6/2002 | Hossain et al. | |
| H2037 H | 7/2002 | Yates et al. | |
| 6,464,704 B2 | 10/2002 | Schmaltz et al. | |
| D465,281 S | 11/2002 | Lang | |
| D466,209 S | 11/2002 | Bon | |
| 6,511,480 B1 | 1/2003 | Tetzlaff et al. | |
| 6,673,092 B1 | 1/2004 | Bacher | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| 7,118,570 B2 | 10/2006 | Tetzlaff et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| 7,329,257 B2 | 2/2008 | Kanehira et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,431,730 B2 | 10/2008 | Viola | |
| D582,038 S | 12/2008 | Swoyer et al. | |
| 7,641,653 B2 | 1/2010 | Dalla Betta et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| 7,854,185 B2 | 12/2010 | Zhang et al. | |
| D630,324 S | 1/2011 | Reschke | |
| 7,896,878 B2 | 3/2011 | Johnson et al. | |
| D649,249 S | 11/2011 | Guerra | |
| D649,643 S | 11/2011 | Allen, IV et al. | |
| 8,147,489 B2 | 4/2012 | Moses et al. | |
| D661,394 S | 6/2012 | Romero et al. | |
| 8,298,233 B2 | 10/2012 | Mueller | |
| D670,808 S | 11/2012 | Moua et al. | |
| 8,343,151 B2 * | 1/2013 | Siebrecht | A61B 17/295 606/51 |
| 8,366,709 B2 | 2/2013 | Schechter et al. | |
| 8,394,096 B2 | 3/2013 | Moses et al. | |
| D680,220 S | 4/2013 | Rachlin | |
| 8,409,246 B2 | 4/2013 | Kerr et al. | |
| 8,409,247 B2 | 4/2013 | Garrison et al. | |
| 8,425,504 B2 | 4/2013 | Orton et al. | |
| 8,425,511 B2 | 4/2013 | Olson | |
| 8,430,877 B2 | 4/2013 | Kerr et al. | |
| 8,439,913 B2 | 5/2013 | Horner et al. | |
| 8,469,716 B2 | 6/2013 | Fedotov et al. | |
| 8,469,991 B2 | 6/2013 | Kerr | |
| 8,469,992 B2 | 6/2013 | Roy et al. | |
| 8,480,671 B2 | 7/2013 | Mueller | |
| 8,491,624 B2 | 7/2013 | Kerr et al. | |
| 8,491,625 B2 | 7/2013 | Horner | |
| 8,491,626 B2 | 7/2013 | Roy et al. | |
| 8,512,336 B2 | 8/2013 | Couture | |
| 8,540,749 B2 | 9/2013 | Garrison et al. | |
| 8,551,091 B2 | 10/2013 | Couture et al. | |
| 8,556,929 B2 | 10/2013 | Harper et al. | |
| 8,568,397 B2 | 10/2013 | Horner et al. | |
| 8,568,408 B2 | 10/2013 | Townsend et al. | |
| 8,585,736 B2 | 11/2013 | Horner et al. | |
| 8,591,510 B2 | 11/2013 | Allen, IV et al. | |
| 8,597,295 B2 | 12/2013 | Kerr | |
| 8,623,018 B2 | 1/2014 | Horner et al. | |
| 8,628,557 B2 | 1/2014 | Collings et al. | |
| 8,641,712 B2 | 2/2014 | Couture | |
| 8,647,343 B2 | 2/2014 | Chojin et al. | |
| 8,652,135 B2 | 2/2014 | Nau, Jr. | |
| 8,663,222 B2 | 3/2014 | Anderson et al. | |
| 8,672,939 B2 | 3/2014 | Garrison | |
| 8,679,098 B2 | 3/2014 | Hart | |
| 8,685,009 B2 | 4/2014 | Chernov et al. | |
| 8,685,021 B2 | 4/2014 | Chernov et al. | |
| 8,685,056 B2 | 4/2014 | Evans et al. | |
| 8,702,737 B2 | 4/2014 | Chojin et al. | |
| 8,702,749 B2 | 4/2014 | Twomey | |
| 8,734,445 B2 | 5/2014 | Johnson et al. | |
| 8,740,898 B2 | 6/2014 | Chojin et al. | |
| 8,745,840 B2 | 6/2014 | Hempstead et al. | |
| 8,747,434 B2 | 6/2014 | Larson et al. | |
| 8,756,785 B2 | 6/2014 | Allen, IV et al. | |
| 8,784,418 B2 | 7/2014 | Romero | |
| 8,795,269 B2 | 8/2014 | Garrison | |
| 8,808,288 B2 | 8/2014 | Reschke | |
| 8,814,864 B2 | 8/2014 | Gilbert | |
| 8,840,639 B2 | 9/2014 | Gerhardt, Jr. et al. | |
| 8,845,636 B2 | 9/2014 | Allen, IV et al. | |
| 8,852,185 B2 | 10/2014 | Twomey | |
| 8,852,228 B2 | 10/2014 | Nau, Jr. | |
| 8,858,553 B2 | 10/2014 | Chojin | |
| 8,864,753 B2 | 10/2014 | Nau, Jr. et al. | |
| 8,864,795 B2 | 10/2014 | Kerr et al. | |
| 8,887,373 B2 | 11/2014 | Brandt et al. | |
| 8,888,771 B2 | 11/2014 | Twomey | |
| 8,888,775 B2 | 11/2014 | Nau, Jr. et al. | |
| 8,898,888 B2 | 12/2014 | Brandt et al. | |
| 8,900,232 B2 | 12/2014 | Ourada | |
| 8,906,018 B2 | 12/2014 | Rooks et al. | |
| 8,920,421 B2 | 12/2014 | Rupp | |
| 8,932,293 B2 | 1/2015 | Chernov et al. | |
| 8,936,614 B2 | 1/2015 | Allen, IV | |
| 8,939,972 B2 | 1/2015 | Twomey | |

(56) References Cited

U.S. PATENT DOCUMENTS

| | | |
|---|---|---|
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,084,608 B2 | 7/2015 | Larson et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,211,657 B2 | 12/2015 | Ackley et al. |
| 9,265,568 B2 | 2/2016 | Chernov et al. |
| 9,333,002 B2 | 5/2016 | Garrison |
| 9,381,059 B2 | 7/2016 | Garrison |
| 9,456,870 B2 | 10/2016 | Chernov et al. |
| 9,498,278 B2 | 11/2016 | Couture et al. |
| 9,498,279 B2 | 11/2016 | Artale et al. |
| 9,504,519 B2 | 11/2016 | Kerr et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 2003/0018332 A1 | 1/2003 | Schmaltz et al. |
| 2003/0109875 A1 | 6/2003 | Tetzlaff et al. |
| 2003/0199869 A1 | 10/2003 | Johnson et al. |
| 2003/0220637 A1 | 11/2003 | Truckai et al. |
| 2003/0229344 A1 | 12/2003 | Dycus et al. |
| 2004/0092927 A1 | 5/2004 | Podhajsky et al. |
| 2005/0070889 A1 | 3/2005 | Nobis et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0154387 A1* | 7/2005 | Moses ............... A61B 18/1442 606/51 |
| 2005/0159745 A1 | 7/2005 | Truckai et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0179499 A1 | 8/2007 | Garrison |
| 2007/0260241 A1 | 11/2007 | Dalla Betta et al. |
| 2008/0215048 A1 | 9/2008 | Hafner et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2009/0302090 A1 | 12/2009 | Shah |
| 2009/0308909 A1 | 12/2009 | Nalagatla et al. |
| 2010/0016857 A1 | 1/2010 | McKenna et al. |
| 2010/0130977 A1 | 5/2010 | Garrison et al. |
| 2010/0179545 A1 | 7/2010 | Twomey et al. |
| 2010/0179547 A1 | 7/2010 | Cunningham et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0054469 A1 | 3/2011 | Kappus et al. |
| 2011/0060314 A1 | 3/2011 | Wallace et al. |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238065 A1 | 9/2011 | Hunt et al. |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083785 A1 | 4/2012 | Roy et al. |
| 2012/0083786 A1* | 4/2012 | Artale ............... A61B 18/1442 606/51 |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0184988 A1 | 7/2012 | Twomey et al. |
| 2012/0184989 A1 | 7/2012 | Twomey |
| 2012/0184990 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0018411 A1 | 1/2013 | Collings et al. |
| 2013/0022495 A1 | 1/2013 | Allen, IV et al. |
| 2013/0030432 A1 | 1/2013 | Garrison et al. |
| 2013/0041370 A1 | 2/2013 | Unger |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |
| 2013/0197503 A1 | 8/2013 | Orszulak |
| 2013/0226177 A1 | 8/2013 | Brandt et al. |
| 2013/0296856 A1* | 11/2013 | Unger ............... A61B 18/1442 606/52 |
| 2014/0214019 A1* | 7/2014 | Baxter, III ......... A61B 17/3201 606/33 |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |

(56) References Cited

U.S. PATENT DOCUMENTS

| | | |
|---|---|---|
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | MCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1* | 9/2014 | Hart .................. A61B 18/1445 606/45 |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0066076 A1 | 3/2015 | Kerr et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2016/0157925 A1 | 6/2016 | Artale et al. |
| 2016/0175031 A1 | 6/2016 | Boudreaux |
| 2017/0128120 A1 | 5/2017 | Cho et al. |
| 2018/0325580 A1 | 11/2018 | Sims et al. |

FOREIGN PATENT DOCUMENTS

| | | |
|---|---|---|
| CN | 102525639 A | 7/2012 |
| DE | 2415263 A1 | 10/1975 |
| DE | 02514501 A1 | 10/1976 |
| DE | 2627679 A1 | 1/1977 |
| DE | 03423356 A1 | 1/1986 |
| DE | 3612646 A1 | 4/1987 |
| DE | 3627221 A1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| EP | 1532932 A1 | 5/2005 |
| EP | 2301468 A1 | 3/2011 |
| EP | 2353535 A1 | 8/2011 |
| EP | 2436327 A1 | 4/2012 |
| EP | 2436330 A1 | 4/2012 |
| EP | 2529681 A1 | 12/2012 |
| EP | 3072467 A1 | 9/2016 |
| JP | 61501068 | 9/1984 |
| JP | 6502328 | 3/1992 |
| JP | 55106 | 1/1993 |
| JP | H0540112 A | 2/1993 |
| JP | 6121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | H0856955 A | 3/1996 |
| JP | 08252263 A | 10/1996 |
| JP | H08289895 | 11/1996 |
| JP | H08317934 | 12/1996 |
| JP | H08317936 | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | H1024051 A | 1/1998 |
| JP | H10155798 A | 6/1998 |
| JP | 1147149 | 2/1999 |
| JP | H1147150 A | 2/1999 |
| JP | H1170124 A | 3/1999 |
| JP | H11169381 | 6/1999 |
| JP | H11192238 | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 A | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 10/1973 |
| WO | 9400059 | 1/1994 |
| WO | 9923933 A2 | 5/1999 |
| WO | 0024330 | 5/2000 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 02080786 A1 | 10/2002 |
| WO | 02080793 A1 | 10/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |
| WO | 2013009758 A2 | 1/2013 |
| WO | 2013022928 A1 | 2/2013 |
| WO | 2013134044 A1 | 9/2013 |
| WO | 2015017991 A1 | 2/2015 |

OTHER PUBLICATIONS

Manufacturing: Materials and Processing, Dec. 19, 2006, The National Academies Press, pp. 1-70 (Year: 2006).*
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz, abandoned.
U.S. Appl. No. 09/591,328, filed Jun. 9, 2000, Thomas P. Ryan.

(56) References Cited

OTHER PUBLICATIONS

U.S. Appl. No. 12/336,970, filed Dec. 17, 2008, Paul R. Sremeich, abandoned.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.

Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Heniford et al. "Initial Results with an Electrothermal Bipolar Vessel Sealer" Surgical Endoscopy (2000) 15:799-801. (4 pages).
"Reducing Needlestick Injuries in the Operating Room" Sales/Product Literature 2001. (1 page).
Levy et al., "Update on Hysterectomy—New Technologies and Techniques" OBG Management, Feb. 2003. (15 pages).
Barbara Levy, "Use of a New Vessel Ligation Device During Vaginal Hysterectomy" FIGO 2000, Washington, D.C. (1 page).
Vallfors et al., Automatically Controlled Bipolar Electrocoagulation—"COA-COMP", Neurosurg. Rev. (1984), pp. 187-190.
Examination Report No. 1 issued in corresponding Australian Application No. 2018201752 dated Aug. 8, 2018, 10 pages.
Extended European Search Report issued in corresponding application No. 18171773.7 dated Oct. 8, 2018, 7 pages.
Canadian Office Action issued in Canadian Application No. 2,997,771 dated Jan. 4, 2019, 3 pages.

* cited by examiner

ELECTROSURGICAL FORCEPS

BACKGROUND

The present disclosure relates to electrosurgical instruments and, more particularly, to electrosurgical forceps for grasping, treating, and/or dividing tissue.

TECHNICAL FIELD

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon has to accurately sever the treated tissue. Accordingly, many electrosurgical forceps have been designed which incorporate a knife configured to effectively sever tissue after the tissue is treated.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

An electrosurgical forceps provided in accordance with aspects of the present disclosure includes a first shaft member, a second shaft member pivotably coupled to the first shaft member, a first jaw member secured to and extending distally from the first shaft member, a second jaw member secured to and extending distally from the second shaft member, and a knife. The first jaw member includes a jaw frame, an insulative spacer disposed on the jaw frame and defining a longitudinally-extending channel, and a tissue-contacting plate disposed on the insulative spacer. The knife is selectively translatable through the first shaft member from a retracted position to an extended position in which the knife extends at least partially between the first and second jaw members. The knife includes a distal edge having a sharp, upper segment and a dull, lower segment depending from the upper segment. The lower segment is configured to abut the insulative spacer when the knife is in the extended position.

In aspects, the lower segment of the distal edge of the knife may protrude distally beyond the upper segment.

In further aspects, the upper segment of the distal edge of the knife may extend at an oblique angle relative to a longitudinal axis defined by the knife, and the lower segment may be perpendicular relative to the longitudinal axis.

In some aspects, the lower segment of the distal edge of the knife may be received in the channel of the insulative spacer, and the upper segment may be received in a longitudinally-extending channel defined by the tissue-contacting plate.

In other aspects, the lower segment of the distal edge of the knife may be configured to abut an inner peripheral surface of the insulative spacer upon the knife moving to the extended position. The inner peripheral surface of the insulative spacer may define an outer periphery of the channel.

In another aspect of the present disclosure, an electrosurgical forceps is provided that includes a first shaft member having a first inner frame, a second shaft member pivotably coupled to the first shaft member, a first jaw member secured to and extending distally from the first shaft member, a second jaw member secured to and extending distally from the second shaft member, a knife, and an elongate shell attached to a lateral side of the first inner frame. The knife is selectively translatable through the first shaft member from a retracted position to an extended position in which the knife extends at least partially between the first and second jaw members. The elongate shell defines a longitudinally-extending passageway configured for slidable receipt of the knife therethrough.

In aspects, the elongate shell may have an inner surface that defines the passageway. The inner surface may be configured to permit movement of the knife along a longitudinal axis defined by the knife and resist lateral and vertical movement of the knife relative to the longitudinal axis.

In further aspects, the elongate shell may be fabricated from plastic.

In other aspects, the knife may have a blade stop protruding outwardly therefrom configured to abut a proximal edge of the elongate shell when the knife moves to the extended position to prevent further distal movement of the knife along the passageway.

In some aspects, the elongate shell may have a connection tab extending laterally therefrom and configured to engage a correspondingly shaped aperture defined in the lateral side of the first inner frame.

In aspects, the elongate shell may have a rectangular shape.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
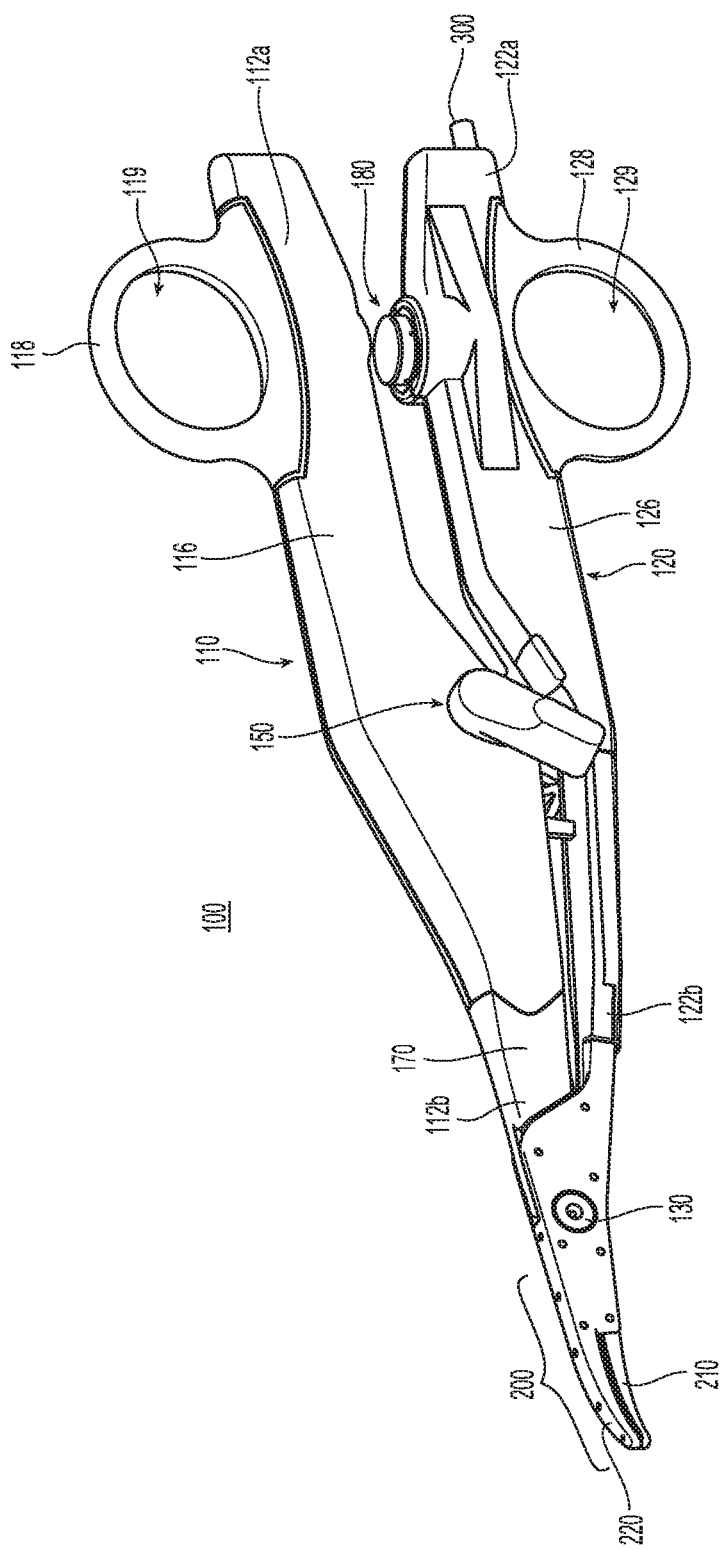
FIG. 1 is a side, perspective view of an electrosurgical forceps provided in accordance with aspects of the present disclosure.
Figure 2:
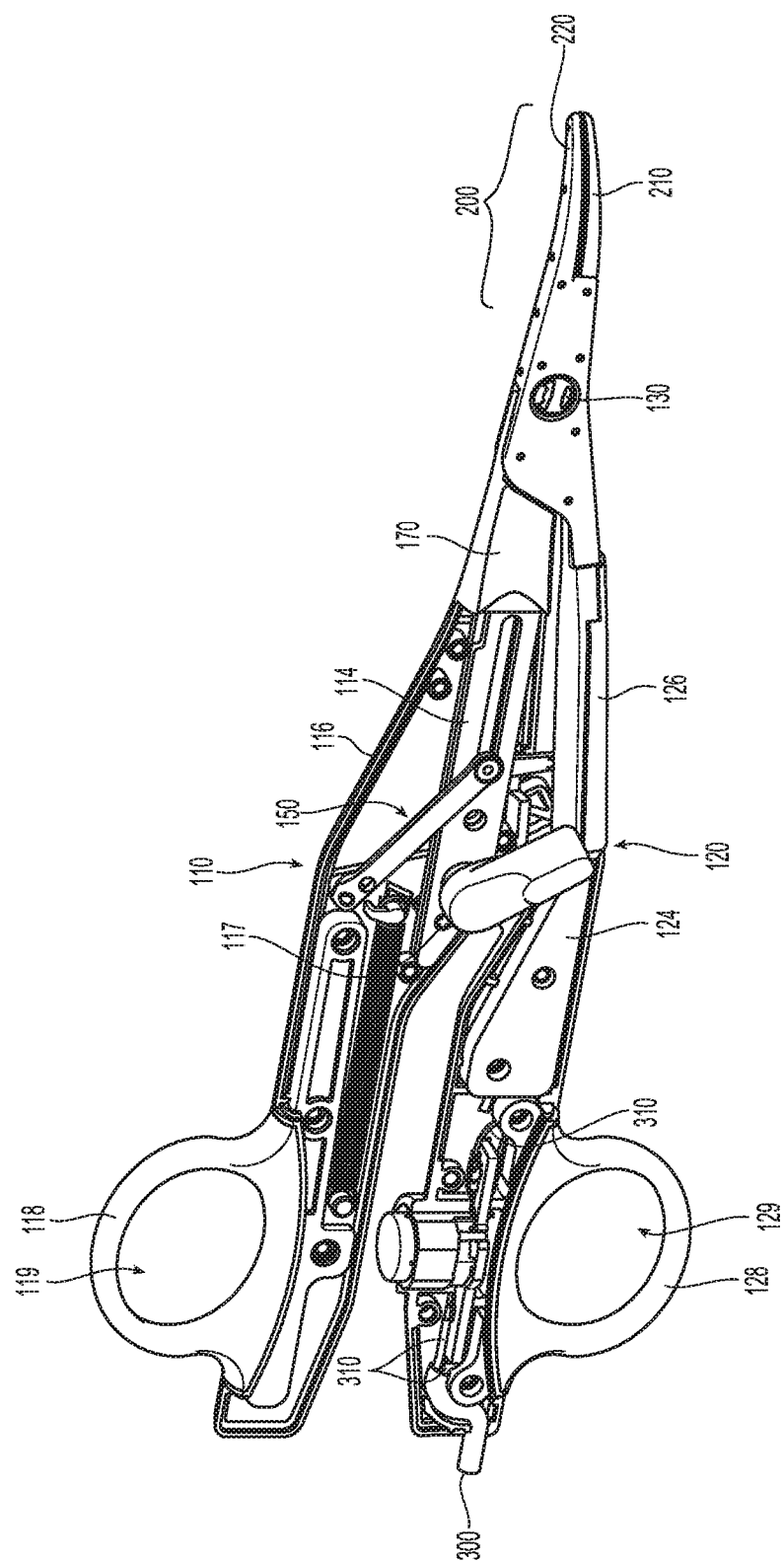
FIG. 2 is a perspective view from one side of the forceps of FIG. 1 with portions of outer housings of first and second shaft members removed to illustrate the internal components therein.

Referring to FIGS. 1 and 2, a forceps 100 provided in accordance with the present disclosure generally includes first and second shaft members 110, 120 and an end effector assembly 200. Shaft members 110, 120 each have a proximal end portion 112a, 122a and a distal end portion 112b, 122b. End effector assembly 200 includes first and second jaw members 210, 220 extending from distal end portions 112b, 122b of shaft members 110, 120, respectively. Forceps 100 further includes a pivot member 130 pivotably coupling first and second shaft members 110, 120 with one another, a knife 140 (FIGS. 3 and 8), a knife deployment mechanism 150 for selectively deploying the knife 140 relative to end effector assembly 200, a knife lockout 170 for inhibiting deployment of knife 140 prior to sufficient closure of jaw members 210, 220, and a switch assembly 180 for enabling the selective supply of electrosurgical energy to end effector assembly 100. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Continuing with reference to FIGS. 1 and 2, each shaft member 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of shaft members 110, 120, respectively. Outer housings 116, 126 enclose and/or operably support the internal components disposed within shaft members 110, 120. More specifically, outer housing 116 of shaft member 110 encloses and supports at least a portion of inner frame 114, knife deployment mechanism 150, and lockout 170, while outer housing 126 of shaft member 120 receives electrosurgical cable 300 and encloses and supports at least a portion of inner frame 124, switch assembly 180, and the lead wires 310 of electrosurgical cable 300. Handles 118, 128 are engaged with outer housings 116, 126 towards proximal end portions 112a, 112b of shaft members 110, 120 and extend outwardly from shaft members 110, 120. Handles 118, 128 define finger holes 119, 129 configured to facilitate grasping and manipulating shaft members 110, 120.

Figure 3:
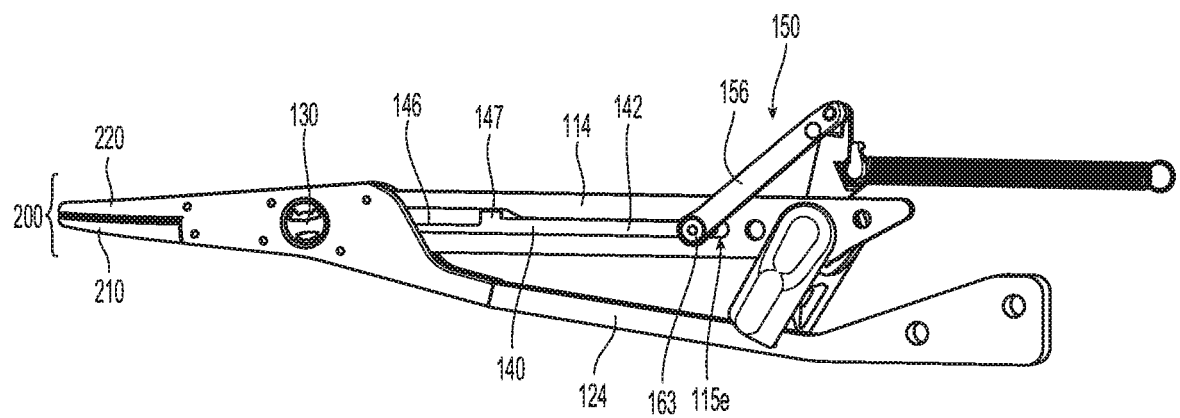
FIG. 3 is a side, perspective view of the forceps of FIG. 1 with portions removed to illustrate a knife within an inner frame of the forceps.
Figure 4:
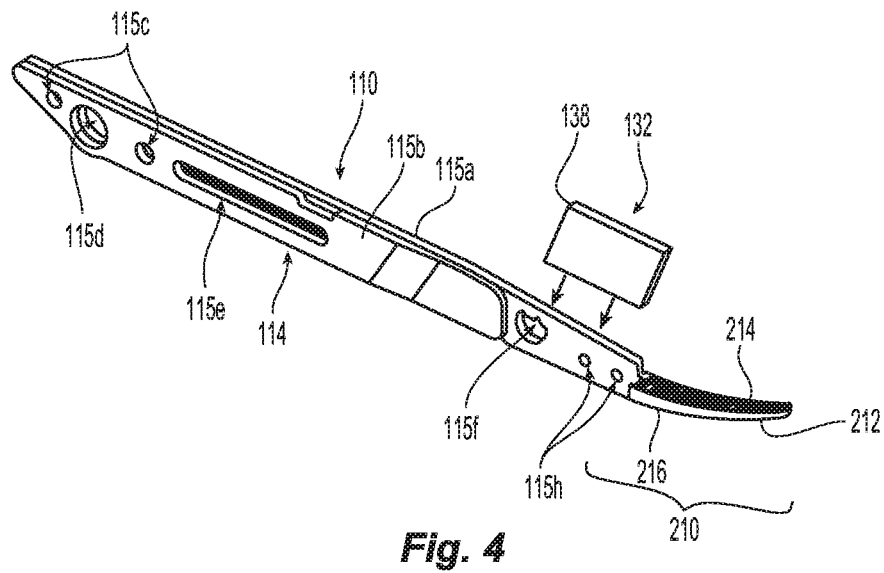
FIG. 4 is a side, perspective view of the inner frame of the first shaft member separated from a knife guide.

Referring to FIGS. 3 and 4, inner frame 114 of shaft member 110 includes a body plate 115a and a reinforcing plate 115b attached to body plate 115a, e.g., via welding, to provide increased lateral stiffness and structural support thereto. In embodiments, reinforcing plate 115b may be welded to body plate 115a in at least two places, e.g., towards the proximal and distal end portions thereof. Inner frame 124 of shaft member 120 and body plate 115a of inner frame 114 of shaft member 110 are pivotably coupled to one another via pivot member 130 such that shaft members 110, 120 are movable relative to one another between spaced-apart and approximated positions to thereby pivot jaw members 210, 220 relative to one another between open and closed positions.

Inner frame 114 defines one or more location apertures 115c, a trigger aperture 115d, and a longitudinal slot 115e that each extends through both body plate 115a and reinforcing plate 115b. The one or more location apertures 115c are configured to receive corresponding posts 117 of outer housing 116 to locate and maintain inner frame 114 in position within outer housing 116. Body plate 115a extends distally beyond reinforcing plate 115b to enable attachment of jaw member 210 thereto, e.g., via staking or other suitable engagement. The portion of body plate 115a that extends distally beyond reinforcing plate 115b further defines a pivot aperture 115f and a pair of longitudinally-spaced connection apertures 115h extending transversely therethrough. Connection apertures 115h are configured for receipt of a pair of correspondingly-shaped tabs 134 of an elongate shell 132 of forceps 100.

Figure 5:
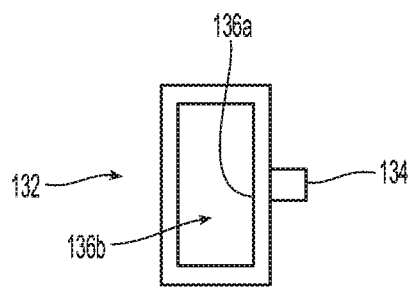
FIG. 5 is a side, cross-sectional view of the knife guide of FIG. 4.
Figure 6:
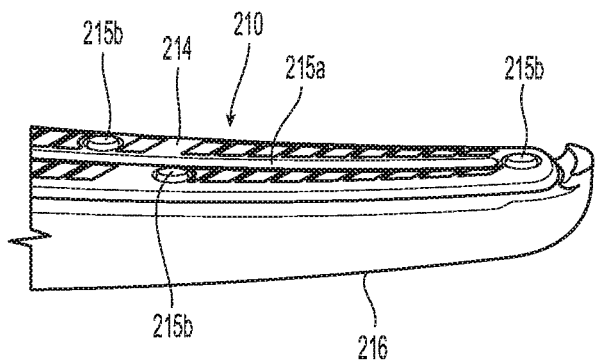
FIG. 6 is a side, perspective view of a jaw member of the forceps.
Figure 7:
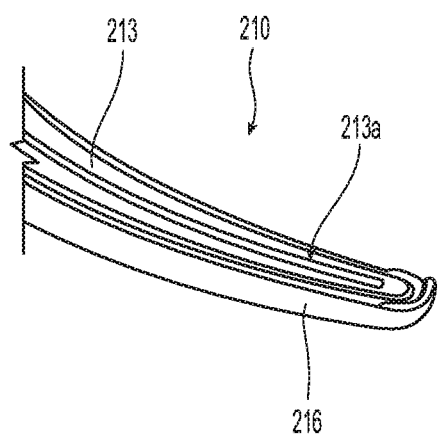
FIG. 7 is a side, perspective view of the jaw member of FIG. 6 with a tissue-contacting plate removed therefrom to reveal an insulative spacer.

With reference to FIGS. 4 and 5, elongate shell 132 of forceps 100 is fabricated from a plastic, such as, for example, a thermoplastic, an elastomer, or any suitable material, and may assume a generally rectangular cross-sectional profile. In embodiments, elongate shell 132 may assume any suitable shape. Elongate shell 132 has an inner surface 136a defining a longitudinally-extending passageway 136b along the length thereof. Passageway 136b is dimensioned for slidable receipt of knife 140. Passageway 136b is open at both the proximal and distal ends of elongate shell 132 to permit movement of knife 140 therethrough. Passageway 136b is sized to permit movement of knife 140 along a longitudinal axis defined by knife 140 while resisting both lateral (e.g., transverse) and vertical (e.g., up and down) movement of knife 140 within passageway 136b. As such, elongate shell 132 guides knife 140 along a linear or substantially linear path from the retracted position to the extended position. Due to the utilization of elongate shell 132, it is not required to form a knife guide slot in inner frame 114, which is typically fabricated from metal (e.g., steel). As such, elongate shell 132 eases the manufacturing of inner frame 114.

Elongate shell 132 has a pair of tabs 134 (only one tab is illustrated) extending laterally therefrom. Tabs 134 are configured for receipt within the pair of apertures 115h in the lateral side of body plate 115a of inner frame 114. Tabs 134 may be sized for a friction-fit engagement within apertures 115h of body plate 115a. In some aspects, elongate shell 132 may be detachably coupled to lateral side of body plate 115a of inner frame 114. In other aspects, elongate shell 132 may be assembled to body plate 115a of inner frame 114 by sliding elongate shell 132 over body plate 115a of inner frame 114.

Knife 140 has a blade stop 147 (FIG. 3) protruding outwardly therefrom configured to abut a proximal edge 138 of elongate shell 132 when knife 140 moves to the extended position. Upon blade stop 147 of knife 140 contacting proximal edge 138 of elongate shell 132, knife 140 is prevented from further advancement. In some aspects, elongate shell 132 may have an internal boss or projection (not shown) extending inwardly from the inner surface 136a thereof into passageway 136b, such that blade stop 147 abuts the projection when knife 140 is advanced to the extended position.

With reference to FIGS. 4 and 6-9, jaw member 110 includes a jaw support or frame 212 (FIG. 4) staked or otherwise engaged, e.g., welded, press-fit, mechanically locked, etc., to portion of body plate 115a that extends distally beyond reinforcing plate 115b. Jaw member 210 further includes an insulative spacer 213 disposed on jaw support 212, an electrically-conductive, tissue-contacting plate 214 supported on insulative spacer 213, and an insulative housing 216. Tissue-contacting plate 214 defines a longitudinally-extending knife channel 215a extending at least partially therethrough and includes one or more stop members 215b disposed thereon and electrically isolated therefrom. Insulative spacer 213 (FIG. 7) also defines a longitudinally-extending channel 213a in alignment with channel 215a of tissue-contacting plate 214. Insulative spacer 213 has an inner peripheral surface 213b that defines an outer periphery of channel 213a. Insulative housing 216 of jaw member 210 is overmolded or otherwise secured about a portion of jaw support 212, insulative spacer 213, tissue-contacting plate 214, and body plate 115a of inner frame 114 of shaft member 110.

Figure 8:
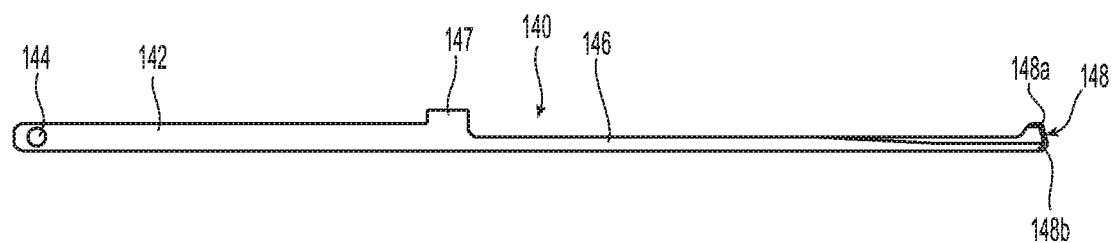
FIG. 8 is a side view of the knife of the forceps.
Figure 9:
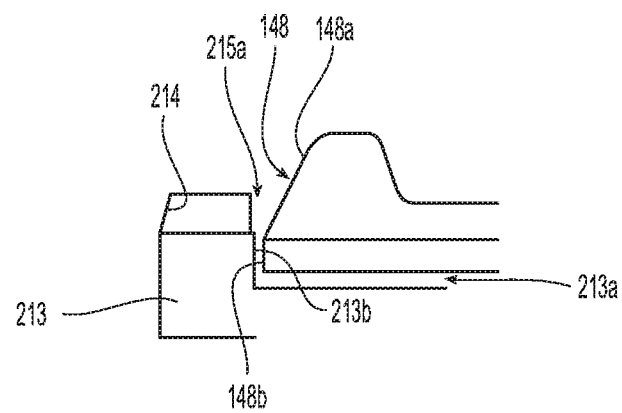
FIG. 9 is a longitudinal cross-sectional view of a distal end of the jaw member of FIG. 6 illustrating the knife in an extended position.

Referring to FIGS. 8 and 9, knife 140 includes a proximal body 142 defining an aperture 144 through which knife 140 is pivotably coupled to a linkage 156 (FIG. 3) of knife deployment mechanism 150 via a pin 163. Knife 140 further includes a distal body 146 defining a lower profile as compared to proximal body 142 and extending distally from proximal body 142. Distal body 146 has a distal edge 148 having a larger profile as compared to distal body 146. Distal edge 148 has a sharp, upper segment 148a, and a relatively dull, lower segment 148b extending from a lower end of upper segment 148a. Upper segment 148a of distal edge 148 may be etched to define an asymmetrically sharpened configuration wherein one lateral side of upper segment 148a of distal edge 148 extends further distally than the opposite side (due to the removal of material from the opposite side during the etching process). Lower segment 148b of distal edge 148 of knife 140 is received in channel 213a of insulative spacer 213, and upper segment 148a of distal edge 148 of knife 140 is received in channel 215a of tissue-contacting plate 214.

Lower segment 148b of distal edge 148 of knife 140 protrudes distally beyond upper segment 148. As such, lower segment 148b abuts a distal end of inner peripheral surface 213b of insulative spacer 213 when knife 140 is in the extended position. In some aspects, upper and lower segments 148a, 148b of distal edge 148 may be co-terminal. Upper segment 148a of distal edge 148 extends at an oblique angle relative to the longitudinal axis of knife 140, and lower segment 148b is perpendicular relative to the longitudinal axis of knife 140. In some aspects, upper and lower segments 148a, 148b of distal edge 148 may extend at various angles relative to one another and/or the longitudinal axis of knife 140.

Figure 10:
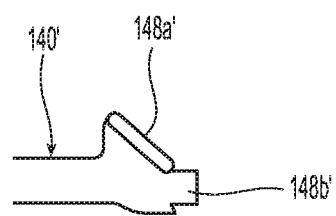
FIG. 10 is side view of a distal end of another embodiment of the knife of the forceps.

With reference to FIG. 10, another embodiment of a knife 140' is illustrated. Knife 140' varies from knife 140 by having a stop 148b' that projects distally from a distal end of knife 140'. Knife 140' has a sharp, cutting edge 148a' that extends at an oblique angle relative to a longitudinal axis of knife 140' and which is set back proximally from stop 148b'. Stop 148b' may be steel, or any suitable material, and have a cylindrical shape or assume any suitable shape. In use, stop 148b' abuts a distal end of inner peripheral surface 213b (FIG. 9) of insulative spacer 213 when knife 140' is in the extended position.

For a detailed description of various components and manners of operating forceps 100 of the present disclosure, reference may be made to U.S. patent application Ser. No. 15/593,672, filed on May 12, 2017, the entire contents of which is incorporated by reference herein.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416 (now U.S. Pat. No. 8,828,023), and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
   a first shaft member;
   a second shaft member pivotably coupled to the first shaft member;
   a first jaw member secured to and extending distally from the first shaft member;
   a second jaw member secured to and extending distally from the second shaft member, the first jaw member including:
      a jaw frame;
      an insulative spacer disposed on the jaw frame and defining a longitudinally-extending channel; and
   a tissue-contacting plate disposed on the insulative spacer and defining a knife channel longitudinally through the tissue-contacting plate, the tissue-contacting plate having a proximal-facing inner edge that defines a distal-most end of the knife channel; and a knife selectively translatable through the knife channel from a retracted position to a fully extended position in which the knife extends between the first and second jaw members, the knife including a distal edge having a sharp, upper segment and a dull, lower segment depending distally from the upper segment, the lower segment configured to abut the insulative spacer when the knife is in the fully extended position, whereby the abutment of the lower segment with the insulative spacer causes the upper segment of the distal edge of the knife to be spaced proximally from the proximal-facing inner edge of the tissue-contacting plate.

2. The electrosurgical forceps according to claim 1, wherein the upper segment of the distal edge of the knife extends at an oblique angle relative to a longitudinal axis defined by the knife, and the lower segment is perpendicular relative to the longitudinal axis.

3. The electrosurgical forceps according to claim 1, wherein the lower segment of the distal edge of the knife is received in the channel of the insulative spacer, and the upper segment is received in the knife channel defined by the tissue-contacting plate.

4. The electrosurgical forceps according to claim 1, wherein the lower segment of the distal edge of the knife is configured to abut an inner peripheral surface of the insulative spacer upon the knife moving to the fully extended position, the inner peripheral surface of the insulative spacer defining an outer periphery of the channel of the insulative spacer.

* * * * *